United States Patent [19]

Hoke

[11] Patent Number: 4,960,496

[45] Date of Patent: Oct. 2, 1990

[54] ATMOSPHERIC HCl MONITOR

[75] Inventor: Steven H. Hoke, Walkersville, Md.

[73] Assignee: The United States of America as represented by the Secretary of the Army, Washington, D.C.

[21] Appl. No.: 324,525

[22] Filed: Mar. 16, 1989

[51] Int. Cl.$^5$ .......................................... G01N 27/416
[52] U.S. Cl. ................................. 204/153.13; 204/409
[58] Field of Search .............................. 204/1 B, 409

[56] References Cited

U.S. PATENT DOCUMENTS

| 4,279,727 | 7/1981 | Scheubeck et al. | 204/1 T X |
| 4,619,739 | 10/1986 | Kanno et al. | 204/1 T |

FOREIGN PATENT DOCUMENTS 1798446 7/1973 Fed. Rep. of Germany .
35049 7/1981 Japan .

OTHER PUBLICATIONS

R. R. Bailey et al., Anal. Chem., vol. 48, No. 12, pp. 1818–1819 (1976).

J. G. Converse et al., ISA Transactions, vol. 15, No. 3, pp. 220–226 (1976).

S. H. Hoke, CPIA Publication 436, pp. 445–449, Nov. 1985.

Primary Examiner—G. L. Kaplan
Attorney, Agent, or Firm—Werten F. W. Bellamy

[57] ABSTRACT

A device for performing rapid determinations on a real-time basis of about three to five seconds of the concentration of HCl in the atmosphere includes an air inlet conduit for sampling the HCl laden air, a pump for introducing trapping solution into the air inlet conduit, a spiral impinger for mixing and combining the air and trapping solution, a separator for separating a portion of the trapping solution and entrained air from the remaining trapping solution, and electrode flow cell for receiving the remaining trapping solution and for determining the chloride ion concentration in the trapping solution. The electrode flow cell includes a measuring electrode having a silver wire having a silver chloride coating inserted in the flow path of the trapping solution. A selector valve is inserted between the separator and the flow cell for alternatively feeding either the separated trapping solution to the flow cell or a standardizing solution to the flow cell.

6 Claims, 1 Drawing Sheet

ATMOSPHERIC HCl MONITOR

BACKGROUND OF THE INVENTION

This invention, in one of its aspects, relates to a process for determining the quantity of hydrogen chloride (HCl) in the atmosphere. In another of its aspects the invention relates to improved apparatus for such determinations. In still another of its embodiments the invention provides a rapid process which, on a real-time basis, that is, without a reaction-time delay, can be relied upon by personnal with a need to enter an area after an HCl-generating event.

There is concern within the military community over the potential health effects from combustion products resulting from the firing of various weapons systems. Of particular interest are the relatively high concentrations of HCl produced by combustion of rocket propellants used in U.S. Army weapons systems such as the STINGER and Multiple Launch Rocket System (MLRS). Some propellants used for rocket fuels are perchlorate-based and form HCl as one of their combustion products. Systems, which use perchlorate-based propellants, create potentially hazardous field exposures for operators. Personnel associated with rocket firings may be exposed to short-term decrements in performance. Monitoring methods used by various agencies and contractors were evaluated in test firings of the STINGER and CHAPARREL rockets. Noticeable limitations in monitoring capability observed during these field testings included the lack of field calibration and the lack of replicate sampling from identical sample points. The primary methods utilized for HCl monitoring were the batch-type midget impinger and the continuous-type Geomet TM HCl monitor. The midget impinger traps all forms of HCl, but it does not provide real-time data. The Geomet TM HCl monitor measures HCl on a real-time basis, but it has not been established that the Geomet TM method detects all forms of HCl. HCl can be present as a gas, as an aerosol, or as HCl adsorbed on particulate matter.

When the STINGER is fired operators remain in the launch area during the launch. In the case of other launches, there is usually a need to re-enter a launch area as soon as possible after a firing. Such personnel need to know how safe such areas are. In order to assess potential health hazards, all forms of atmospheric HCl must be monitored on a real-time basis. There is an obvious and urgent need to develop an atmospheric monitor that detects all forms of HCl on a real-time basis in order to accurately evaluate potential health hazards. With such information, recommendations can be made relative to personnel protection and weapons design.

In 1985, at the JANNAF Safety & Environmental Protection Subcommittee Proceedings I presented a method for determining hydrogen chloride in the atmosphere on a near real-time basis. The presentation was published by the Chemical Propulsion Information Agency in CPIA Publication 436, November, 1985 herein incorporated by reference. The method described incorporated the principles of both midget impinger techniques and flow injection analysis. The impinger techniques were designed to extract HCl gas, aerosol forms of HCl, and HCl adsorbed on particulate matter into a trapping solution. Flow injection analysis allowed for continuous sampling and replenishing of the impinger reservoir of trapping solution. By using small diameter tubing and reducing quiescent zones, or dead volumes, throughout the system, it was possible to approach, although not as closely as desired, real-time monitoring of total HCl. A response time, the time for obtaining results, of 5 seconds, although not attained, was desirable since such a period would coincide with the frequency of normal breathing.

In my 1985 process air was drawn in through a miniature impinger, at approximately 1,000 mL/min. Trapping solution (water or a buffering solution) was pumped into the impinger at its front end. By the time this mixture reached the end of the impinger, the trapping solution had extracted about 95 percent of the total concentration of HCl in the atmosphere sample. The air/liquid mixture was separated and air was drawn off, while the trapping solution was withdrawn for testing. In testing, the trapping solution, and chloride reagent containing $Hg(SCN)_2$ and $Fe(NO_3)_3$, were mixed, and the mixture was passed through a 37° C. temperature bath and into a flow cell. Therein the absorbance was measured at 480 nm with a colorimeter. The response was monitored by a strip chart recorder. There was a delay of about 15 seconds from the time HCl entered the miniature impinger until a deflection was noted on the strip chart recorder. Another period of roughly 13 to 15 seconds was required for a monitor to reach 90 percent of total response. The response time thus was longer than the desired 5 seconds, and while the monitor responded to all forms of atmospheric HCl, the HCl response was from about 1 to 100 ppm. It was reproducible, but non-linear. There is, then, a need for a monitor meeting such criteria as a response time of 5 seconds or less, and a linear, more accurate HCl response. For this reason the 1985 monitor was not considered finally developed. By this invention a fully developed process, and apparatus for carrying out the process, is provided meeting those criteria.

SUMMARY OF THE INVENTION

I know of no HCl monitor which responds to all forms of HCl on a near-real-time basis. The reason for this is that no process used for detecting atmospheric HCl utilizes the principles of both midget impinger techniques and flow injection analysis as I described in my 1985 presentation. In that process atmospheric air in which HCl is present is continuously mixed in a miniature impinger with an aqueous trapping solution which extracts in its aqueous phase at least 95 percent of the HCl. The air is then continuously separated from the HCl-containing trapping solution, and the trapping solution aqueous phase is analyzed continuously for chloride. In the present improvement the response time more nearly approaches real-time conditions and the chloride analysis is more accurate. This improvement entails a chloride ion selective electrode adapted for fluid flow therethrough and capable, during such fluid flow, of continuously generating an electrical potential corresponding to ionic activity of the chloride ion. The chloride-containing trapping solution flowing through the electrode is electronically measured and the potential from the electrode is recorded. The measured potential can then be correlated to a specific concentration of HCl.

DESCRIPTION OF PREFERRED EMBODIMENT

The Geomet TM HCl monitor responds well to gaseous HCl in ambient air on a real-time basis. But its response to HCl aerosols and particle-adsorbed HCl is in doubt. The reason for this is that it does not include impinger techniques. Impinger techniques designed to extract HCl gas, aqueous aerosol forms of HCl, and HCl adsorbed on particulate matter into a trapping solution. Flow injection analysis on the other hand allows for continuous sampling and replenishment of the impinger trapping solution reservoir. By decreasing tubing diameter and reducing dead volumes throughout the system, one can approach real-time monitoring of total HCl. How both midget impinger techniques and flow injection analysis permit more accurate, real-time, analysis will be apparent from a description of a preferred embodiment of the invention in conjunction with the accompanying drawings.

By referring to FIG. 1, the operation of the invention will now be described. Air (A), containing all forms of HCl, is drawn through a spiral glass impinger (B) at about 1 L/min. At the front of the impinger, trapping solution (C), consisting of 0.1 M NaNO$_3$, is introduced into a tee (D) at the rate of 3 mL/min by a peristaltic pump (E). The air draws the trapping solution through the impinger (B) rapidly and HCl present in any form is extracted from the air into the trapping solution. At the end of the impinger another tee (F) is used to separate the air from trapping solution (C). Air is withdrawn horizontally by an air pump (G) from tee (F) through a trap (H). The trapping solution is drawn downwardly at a rate of 2.5 mL/min due to the suction of peristaltic pump (E). The 0.5 mL/min of excess trapping solution that enters the impinger is drawn off with the air and collected in trap (H). When trapping solution (C) leaves impinger (B) it contains all HCl originally in the air. The trapping solution flows through a selector valve (I) and the chloride ion it contains is detected potentiometrically by a flow-through chloride electrode (J). The voltage from the electrode is measured with a pH meter (K) and monitored on a strip chart recorder (L). After the trapping solution is drawn through electrode J, it is pumped through peristaltic pump (E) into a waste container (M). By means of selector valve (I) and chloride standards (N), the system can be calibrated. The monitor weighs about 15 pounds, with overall dimensions of 7×14×18 inches, and it is operated from a single 110 volt alternating current outlet.

Figure 2:
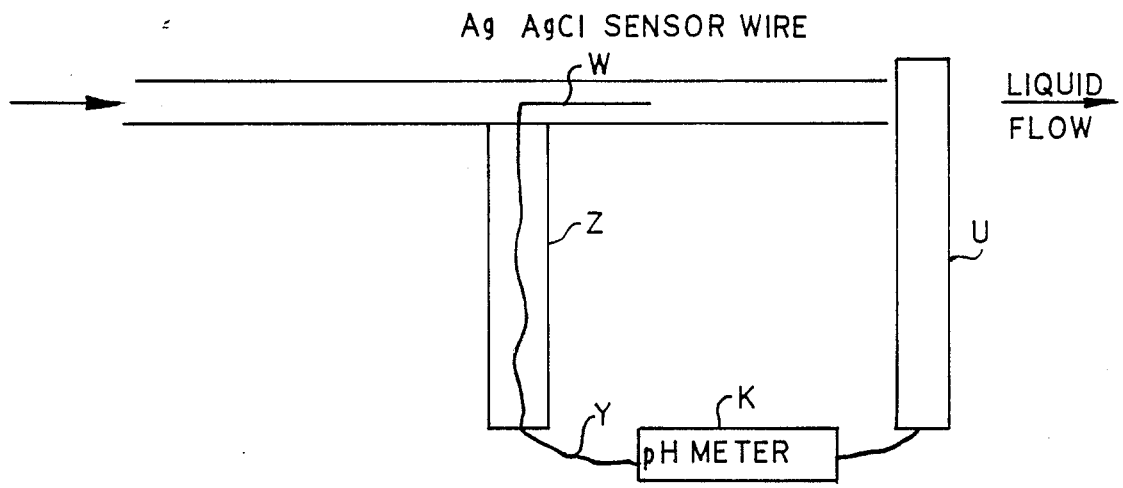
FIG. 2 is a diagrammatic representation of one form of flow-through cell incorporated in the monitor of the invention.

Originally, the HCl monitor utilized a commercially available chloride electrode and flow cell. However it was found that a conventional batch process electrode was unsuitable. Due to undesirable response characteristics this flow cell was modified in an effort to enhance its accuracy. It was thought that improved flow would upgrade the electrode's response. Accordingly it was converted to a flow-through cell, but it was difficult to operate the modified cell without some leaking, and other problems, such as quiescent zones and tiny air bubbles which worked their way into the line from the miniature impinger. The air bubbles were carried through the cell, disrupting flow. With such problems in mind, a miniature flow cell was designed. This microelectrode is shown in FIG. 2. The design includes a tubular flow channel (V) with an electrode (W) consisting of a small silver/silver chloride wire permanently projecting into the channel. The tubular diameter is so small that it mitigates flow disruptions alluded to, and the electrode is in perfect contact with the trapping solution at all times. The wire electrode is connected to the pH meter (K) and reference electrode (U) by lead wires (Y) through insulated and shielded stem (Z). This microelectrode is extremely accurate, with the air bubble problems and dead spaces having no effect.

EXAMPLE

Figure 1:
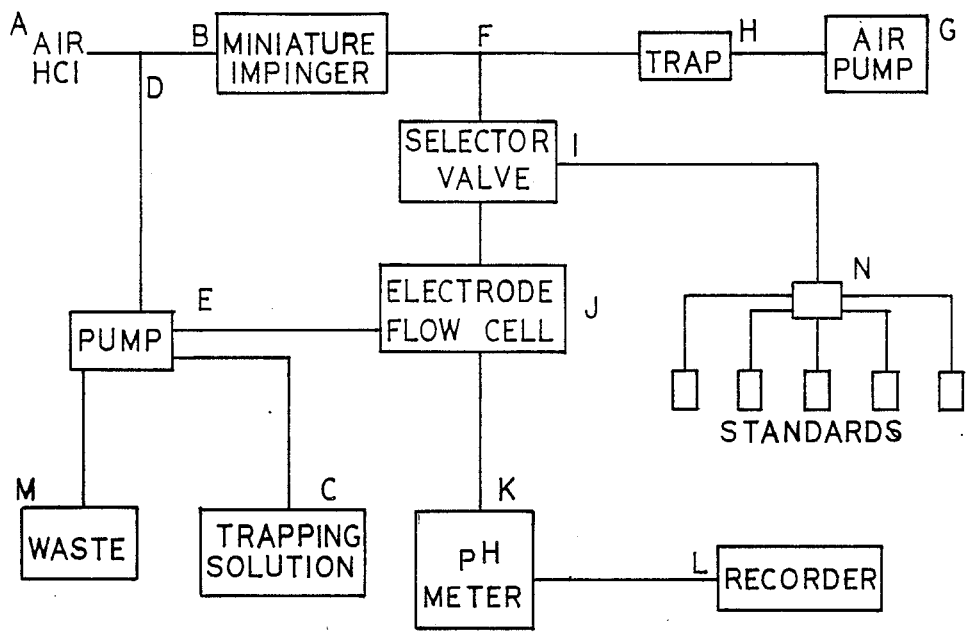
FIG. 1 is a schematic diagram showing the HCl monitor of the invention.

Using the electrode described in conjunction with FIG. 2, in the monitor whose operation is set forth in FIG. 1, HCl-containing gas samples were tested. The system was found to be functioning properly when a near-Nerstian response to HCl gas was observed to be from 1 mg to 2000 mg per cubic meter (about 55 mV response for a ten-fold change in concentration). It also responded well to aqueous HCl aerosols. A delay time of less than 3 seconds and a response time of 3.5 seconds were attained. Delay time is defined as the time required to see an observable response after HCl first enters the system. Response time is defined as the time that elapses from the first system response to chloride until it reaches 90 percent of the total response. The monitor can be calibrated in less than 3 minutes with the five NaCl standards (N), each prepared in 0.1 M NaNO$_3$.

In the following Table, for various concentrations of HCl gases and aerosols, results obtained with the monitor of this invention (designated BRDL monitor herein) are compared with the impinger (batchwise) procedure recommended for HCl determinations by the U. S. Department of Health, education, and Welfare, Public Health Service, Center for Disease Control of the National Institute for Occupational Safety and Health (Hydrogen Chloride, Method No. S246).

TABLE

| Comparison of Impinger and BRDL Monitor | | |
|---|---|---|
| AEROSOL (Nominal HCl) | IMPINGER (mg/m) | BRDL MONITER (mg/m) |
| 500 mg/L | 21.4 | 16.9 |
| 1000 mg/L | 29.0 | 28.5 |
| 2000 mg/L | 69.2 | 70.7 |
| 3000 mg/L | 79.8 | 89.8 |
| 4000 mg/L | 132.7 | 125.5 |
| 8000 mg/L | 341.2 | 342.4 |
| GAS SAMPLE | | |
| 1 | 6.2 | 6.1 |
| 2 | 23.8 | 22.0 |
| 3 | 152.0 | 145.3 |

Referring to the Table, it can be seen that there is substantial agreement between the impinger and the BRDL monitor for both aerosol and gaseous HCl samples.

From the foregoing example and table it is apparent that the BDRL HCl monitor was designed to respond to all forms of atmospheric HCl on a real-time basis and to be fieldable. It is fairly light and portable, and the center of gravity has been kept low to provide stability during operation. It opens like a suitcase for easy access to components and routine maintenance, and calibration can be performed easily and rapidly. It is rugged since it has few glass components.

Having been given the teachings of this invention variations and ramifications will occur to those skilled in this art. Thus, even though one form of flow-through microelectrode has been described, other forms are obviously feasible. Further, whereas five standards have been illustrated for calibrating the monitor, a three standard method, or any other calibration method can be employed. A datalogger or strip chart recorder can be connected to output jacks for remote monitoring of HCl. The monitor can operate unattended for up to eight hours before trapping solutions need be replenished. In addition, whereas a 110 volt alternating current power supply has been described, battery power can be utilized if desired. These and other modifications occurring to those skilled in the art are deemed to be within the scope of this invention.

What is claimed is:

1. A monitoring device for rapid monitoring of atmospheric HCl comprising:
   an air inlet conduit for introducing HCl laden air into the monitoring device;
   means for introducing a trapping solution into the air inlet conduit for mixing with the HCl in the HCl laden air, the means for introducing the trapping solution including a first pump for pumping the trapping solution into the air inlet conduit;
   impinger means connected to the air inlet conduit and located downstream of the means for introducing trapping solution for causing the HCl in the HCl laden air to mix with the trapping solution;
   separating means connected to and located downstream of the impinger means for separating air from the trapping solution, said separating means having an inlet connected to the impinger means, and first and second outlets;
   air pump and liquid trap means connected to the first outlet of the separating means for drawing the air and a portion of the trapping solution from the separating means, the liquid trap means inserted between the first outlet of the separating means and the air pump, the air pump and liquid trap means operating to create a suction in the first outlet of the separating means for drawing off a portion of the trapping solution which carries off substantially all air from the separating means, so that air is removed from the remaining portion of the trapping solution flowing from the second outlet of the separating means;
   an electrode flow cell connected to the second outlet of the separating means for receiving the remaining portion of the trapping solution and for determining the concentration of chloride ion in the remaining portion of the trapping solution; and
   means for drawing trapping solution from the second outlet of the separating means and through the electrode flow cell.

2. The monitoring device according to claim 1, wherein the electrode flow cell comprises a test electrode having a silver chloride coated silver wire inserted into the flow path of the trapping solution to measure the chloride ion concentration, a reference electrode communicating with the flow path of the trapping solution, and a pH meter connected between the test electrode and the reference electrode.

3. The monitoring device according to claim 1, further comprising:
   standardizing means in the form of standardizing solutions for flowing through the electrode flow cell to calibrate and standardize the electrode flow cell; and
   a selector valve disposed between the separating means, the electrode flow cell, and the standardizing means, the selector valve having a first position wherein trapping solution in the separating means flows to the electrode flow cell and a second position where the flow of trapping solution to the electrode flow cell is stopped and the standardizing solutions flow to the electrode flow cell.

4. The monitoring device according to claim 1, wherein the electrode flow cell comprises a test electrode having a silver chloride coated silver wire inserted into the flow path of the trapping solution to measure the chloride ion concentration, a reference electrode communicating with the flow path of the trapping solution, and a pH meter connected between the test electrode and the reference electrode;
   and further comprising:
   standardizing means in the form of standardizing solutions for flowing through the electrode flow cell to calibrate and standardize the electrode flow cell; and
   a selector valve disposed between the separating means, the electrode flow cell, and the standardizing means, the selector valve having a first position wherein trapping solution in the separating means flows to the electrode flow cell and a second position where the flow of trapping solution to the electrode flow cell is stopped and the standardizing solutions flow to the electrode flow cell.

5. A monitoring device for monitoring the hydrogen chloride concentrations in air on a real-time, continuous basis of from about three to five seconds, comprising:
   an air inlet conduit for introducing hydrogen-chloride laden air into the monitoring device;
   a container of trapping solution for mixing with the hydrogen chloride laden air;
   a first pump connected to the air inlet conduit and the container of trapping solution for adding the trapping solution to the air inlet conduit;
   an impinger connected to the air inlet for mixing the hydrogen-chloride laden air with the trapping solution;
   a separator connected to the impinger, the separator having an inlet and first and second outlets;
   a fluid trap and air pump connected in series to the first outlet of the separator for drawing-off the air and a portion of the trapping solution which carries off substantially all air from the separating means, so that air is removed from the remaining portion of the trapping solution flowing from the second outlet of the separating means;
   an electrode flow cell connected to the second outlet of the separator for determining the chloride ion concentration in the trapping solution, wherein the electrode flow cell includes a measuring electrode, a reference electrode and a meter for measuring the electrical potential between the electrodes to determine the chloride ion concentration, and wherein the meter measures the electrical potential of a particular sampling of from within about three to five seconds after the particular sample of hydrogen-chloride laden air is introduced into the air inlet conduit;
   a container of standardizing solutions connected to the electrode flow cell for selectively introducing standardizing solution into the electrode flow cell;
   a selector valve connected to the second outlet of the separator, the container of standardizing solution and the flow cell, wherein the selector valve rotates between a first position wherein the trapping solution from the second outlet of the separator flows into the flow cell, and a second operative position wherein the standardizing solution flows into the electrode flow cell and the flow of trapping solution into the electrode flow cell is terminated; and pump means connected to the outlet of the electrode flow cell for drawing the trapping solution through the electrode flow cell.

6. A process for determining the atmospheric HCl in a sample on a continuous basis and within about three to five seconds of the taking of a sample comprising the steps of:

introducing a sample of HCl laden air into an air inlet conduit;

mixing a trapping solution with the HCl laden air for separating chloride ions from the air;

separating the air and a portion of the trapping solution from the remaining portion of the trapping solution so that the remaining portion of trapping solution is substantially free of air, wherein the air and portion of trapping solution are drawn through a fluid trap and air pump means with the portion of trapping solution being separated from the air in the flow trap means and serving to carry the air away from the remaining portion of trapping solution;

introducing the remaining portion of trapping solution into an electrode flow cell containing a measuring electrode for measuring the potential of the chloride ion in the trapping solution and a reference electrode;

measuring the potential difference between the measuring electrode and the reference electrode to determine the chloride ion concentration; and drawing the remaining portion of trapping solution through and away from the electrode flow cell, wherein the process for determining the atmospheric HCl in the sample occurs within about three to five seconds.

* * * * *